(12) United States Patent
Franssen et al.

(10) Patent No.: US 7,214,861 B2
(45) Date of Patent: May 8, 2007

(54) ENOD2 GENE REGULATORY REGION

(75) Inventors: Henk J. Franssen, Nijmegen (NL); Anton H. Blsseling, Ma Ede (NL)

(73) Assignee: Mycogen Plant Science, Inc., San Diego, CA (US)

( * ) Notice: Subject to any disclaimer, the term of this patent is extended or adjusted under 35 U.S.C. 154(b) by 374 days.

(21) Appl. No.: 10/751,014

(22) Filed: Jan. 2, 2004

(65) Prior Publication Data

US 2004/0172676 A1    Sep. 2, 2004

Related U.S. Application Data

(63) Continuation of application No. 09/564,142, filed on May 3, 2000, now abandoned, which is a continuation of application No. 08/859,555, filed on May 20, 1997, now abandoned, which is a continuation of application No. 08/411,062, filed on Mar. 27, 1995, now Pat. No. 5,631,358, which is a continuation of application No. 07/214,297, filed on Jul. 1, 1988, now abandoned.

(51) Int. Cl.
*C12N 15/63* (2006.01)
*C12N 15/82* (2006.01)

(52) U.S. Cl. ........................ 800/312; 800/287
(58) Field of Classification Search ............... 800/278, 800/287, 312; 536/23.1, 24.1
See application file for complete search history.

(56) References Cited

U.S. PATENT DOCUMENTS 4,886,753 A    12/1989    Marcker et al.

OTHER PUBLICATIONS

Widholm J. M., TibTech, Nov. 1988, vol. 6, pp. 265-266.*
McCabe et al. Bio/Technology vol. 6, Aug. 1998, pp. 923-926.*
Hinchee et al. Bio/Technology vol. 6, Aug. 1998, pp. 915-921.*
Park Y. D. et al., Plant Journal Feb. 9, 1996, (2): pp. 183-194.*
Terce-Laforgue T. et al. Plant Mol. Bio. 1999, vol. 39: pp. 551-564.*
Alberts et al., Molecular Biology of the Cell (1983), p. 769.
Franssen et al., Proc. Natl. Acad. Sci. (1987), p. 4495-4499, vol. 84.
Fuller et al., Proc. Natl. Acad. Sci. (1983), p. 2594-2598, vol. 80.
Fuller et al., Plant Mol. Biol. (1984), p. 21-28, vol. 3.
Govers et al., Nature (1986), p. 564-566, vol. 323.
Govers et al., Plant Molecular Biology (1987), p. 425-435, vol. 8.
Jensen et al., Nature (1986), p. 669-674, vol. 321.
Mauro et al., Nucl. Acids Res. (1985), p. 239-249, vol. 13.
Rieger et al., Glossary of Genetics and Cytogenetes (1976), p. 462, Springer Verlag.
Watson et al., "Recombination at the Molecular Level," Molecular Biology of the Gene, 4h Ed. (1987), p. 313.

* cited by examiner

*Primary Examiner*—Russell P. Kallis
(74) *Attorney, Agent, or Firm*—Saliwanchik, Lloyd & Saliwanchik

(57) ABSTRACT

A plant promoter is provided comprising the regulatory region of a legume Enod2 gene, a gene expressed in nodule tissue of legumes in the early stages of nodulation. The promoter operates to express foreign genes under its control in developing nodules. The sequence of two soybean Enod2 genes with their regulatory regions is provided.

8 Claims, 9 Drawing Sheets

Nucleotide Sequence of Enod2a Genomic Clone

```
                        GGATCCTTACACAGGCCAGACATCCCCAAGTTCTCA        36
                        BamHI
AATAAGACAAATTTGGTTGTTCTTTTCTTAATATTTCACAGGGAGATGTTCTGTCTTTTG        96
ATTTGGGGATTTCATTTAGCACATAACAAACAGTTAACAAAATTTCGCCCCACCAAAAAG       156
ATGTTGCACTAGAACTCAACATAGTAGCTACAACTAATTCTGTAAAAGTTCTGTTCTTTC       216
TTTCAGCTTTACCGTTCATTTCAGGTGAATATGGAGCAGTTGTTTCATGTATGATTCCAT       276
GCAAATTATAAAACTCATTAAACAAACTGGAATCATACTCTGTGCCTCTATCACTTCGAA       336
GTTTCTTAATTTTCTTATTGAATTGATTTTCAATTTCTGTTACAAATAACTTAAACATGT       396
CAAGCGCTTCACTTTTATTTTTCATAAGATATACATATATATATAATCAGAGCAGTCATC       456
AATAAAAGTGATAAAATATCGTTTTCCATTTCTGGTCAACGTTCCATCAAATTCACATAT       516
ATCAGAATGTATTAAATCCAATGGCTCAGATTCTTTAACTACTGATTTTTGTGATTTTTT       576
AGTTATTTTAGATTGACTGCAAAAAACACACTTTTCAAAGTGATTTGAAGATAGCTTTGG       636
AATAAAACCTAAGTTACTCATATTAGATATGCAACGACTATTTATATGACAAAGTCTAGA       696
ATGCCAGAATTAAAAATCACACAGCATGTAAGCAGAAGGAGAAACTTTATTAATATCAAGA      756
TTCAATTTGAACATGCCATCAGTGGCGTACCCTTTCCCTACAAATACCCCATTCTTGGTC       816
AAAGTAAATAAATCTGCACCTATGGTCTGAGTAAACCCAGCCTTGTTTAAAAGAAAACCA       876
GAAACCAGATTCTTTCTCATCTCTGGAGTATGCATCACATCTTTGAGAATCAAAGTCTTT       936
CCAGAGGTAAACTTCAGTTCAACATCTCCAGTTCTAGCAACAGTAGTGGTGTGGGAATCA       996
```

FIG. 2A

```
CCCAACAACACTTTCTTATTTTCAACATTCGTGTATGTTTTAAACATAGCATGATCTTTA      1056
                                                  Sau3A

TACTTGTATTTTTTTTTGTTTTAGTTTCTATACTTAAAAATTCTGTTTTATTATTTTTA      1116

CGCCTTAGTTTTCTAGCAATCTAAAACTGATATAAAATAGAAGTATAACGACTAAAACAT     1176

AAAAAAAAAAATTGTATAAAAAATAAAGCATATAGCTTTCATTCATATATAAGAACTAA      1236

ACTGAAATACCAGTGTAAGTATAAGAACTAATCGATAAATTAAGCCAAATTAAGGGTACA     1296

TATTATTTTTAAGAAAATTAGGCCGGGTATATATTTTTAAAAAGGACTATACACTATGTG    1356

ACGATAGAAATAATAGGTATGTAGATGTATGTTAAGTATTTTCTAATGTGTTTTTTACTT    1416

TCTCTATCACACTTGTTATTTTCTCACTATTTTTTTCTCTTGTTTCTCTGTTATTTTCAC     1476

TCTAAAACTGGAGTAATATGTTTATGACTACAACACATTTTGACATGACTTAGGATTAAC    1536
              ‾‾‾                                 Hind3

ATATATTATGATAAAATAACTAAAGATTGATAACCTTGATAGAAAAGCTTCTCATGTCTC   1596
    TS ± 20

CTCTCCCTATAAGTAGTTTCCCATTGTTATCACTTTTCATCAGCACAAGCTAAGACATGA   1656
                                                          ORF1 M

CTTCTGTACTACACTACTCACTCCTGCTGCTCCTGCTTGGAGTGGTGATTCTCACCACTC   1716
 T  S  V  L  H  Y  S  L  L  L  L  L  G  V  V  I  L  T  T

CAGTGCTAGCTAATTTGAAGCCACGCTTCTTCTATGAGCCTCCTCCAATTGAGAAACCCC   1776
 P  V  L  A  N  L  K  P  R  F  F  Y  E  P  P  P  I  E  K  P
                              OFR2  M  S  L  L  Q  L  R  N  P

CCACCTATGAACCTCCACCATTTTATAAGCCCCCATACTACCCACCACCAGTGCACCACC   1836
 P  T  Y  E  P  P  P  F  Y  K  P  P  Y  Y  P  P  P  V  H  H
   P  P  M  N  L  H  H  F  I  S  P  H  T  T  H  H  Q  C  T  T

CTCCACCAGAGTACCAACCACCCCATGAAAAAACACCACCTGAGTATCTACCTCCTCCTC   1896
 P  P  P  E  Y  Q  P  P  H  E  K  T  P  P  E  Y  L  P  P  P
   L  H  Q  S  T  N  H  P  M  K  K  H  H  L  S  I  Y  L  L  L

ATGAGAAACCACCACCAGAATACCTACCTCCTCATGAGAAACCGCCACCAGAATACCAAC   1956
 H  E  K  P  P  P  E  Y  L  P  P  H  E  K  P  P  P  E  Y  Q
   M  R  N  H  H  Q  N  T  Y  L  L  M  R  N  R  H  Q  N  T  N
```

FIG. 2B

```
CTCCTCATGAGAAACCACCCCATGAGAATCCACCACCGGAGCACCAACCACCTCATGAGA      2016
 P  P  H  E  K  P  P  H  E  N  P  P  P  E  H  Q  P  P  H  E
   L  L  M  R  N  H  P  M  R  I  H  H  R  S  T  N  H  L  M  R

AGCCACCAGAGCACCAACCACCTCATGAGAAGCCACCACCAGAGTATGAACCACCTCATG      2076
 K  P  P  E  H  Q  P  P  H  E  K  P  P  P  E  Y  E  P  P  H
   S  H  Q  S  T  N  H  L  M  R  S  H  H  Q  S  M  N  H  L  M

AGAAACCACCACCAGAATACCAACCACCTCATGAGAAGCCACCACCAGAATACCAACCAC      2136
 E  K  P  P  P  E  Y  Q  P  P  H  E  K  P  P  P  E  Y  Q  P
   R  N  H  H  Q  N  T  N  H  L  M  R  S  H  H  Q  N  T  N  H

CTCATGAGAAACCACCACCAGAATACCAACCACCTCATGAGAAGCCACCACCAGAGCACC      2196
 P  H  E  K  P  P  P  E  Y  Q  P  P  H  E  K  P  P  P  E  H
   L  M  R  N  H  H  Q  N  T  N  H  L  M  R  S  H  H  Q  S  T

AACCACCTCATGAGAAGCCACCAGAGCACCAGCCACCTCATGAAGCCACCACCAGAGT        2256
 Q  P  P  H  E  K  P  P  E  H  Q  P  P  H  E  K  P  P  P  E
   N  H  L  M  R  S  H  Q  S  T  S  H  L  M  R  S  H  H  Q  S

ATCAACCACCTCATGAGAAACCACCACCAGAATACCAACCTCCTCAAGAAAAGCCACCAC      2316
 Y  Q  P  P  H  E  K  P  P  P  E  Y  Q  P  P  Q  E  K  P  P
   I  N  H  L  M  R  N  H  H  Q  N  T  N  L  L  K  K  S  H  H

ATGAAAAACCACCGCCAGAATACCAACCTCCTCATGAAAAGCCACCACCAGAACACCAAC      2376
 H  E  K  P  P  P  E  Y  Q  P  P  H  E  K  P  P  P  E  H  Q
   M  K  N  H  R  Q  N  T  N  L  L  M  K  S  H  H  Q  N  T  N

CTCCCCATGAAAAGCCACCACCAGTGTACCCACCCCCTTATGAGAAACCACCACCAGTGT      2436
 P  P  H  E  K  P  P  P  V  Y  P  P  P  Y  E  K  P  P  P  V
   L  P  M  K  S  H  H  Q  C  T  H  P  L  M  R  N  H  H  Q  C

ATGAACCCCCTTATGAGAAGCCACCCCCAGTAGTGTATCCACCTCCTCATGAGAAACCAC      2496
 Y  E  P  P  Y  E  K  P  P  P  V  V  Y  P  P  P  H  E  K  P
   M  N  P  L  M  R  S  H  P  Q  *  (SEQ ID NO:3)

CCATTTATGAGCCACCGCCATTGGAGAAGCCACCGGTCTACAATCCCCCACCTTATGGCC      2556
 P  I  Y  E  P  P  P  L  E  K  P  P  V  Y  N  P  P  P  Y  G

GCTATCCACCATCCAAGAAAAACTAATAACCACTTGCCTGCGTCACATGTTTTGGTCTAC      2616
 R  Y  P  P  S  K  K  N  *  (SEQ ID NO:2)

TCAAACTTAGACCTGCCCTTTGTCATATAAAGCTTTCTGTTTCTGTTTAAGATCTCAAGT      2676
                                Hind3

ACAATATGTCCCTTCTGCATGCACTACTTCTTCAAAATAAAGGCTTTATGCCTATGTATA      2736

ATACTCTACTTTAATTCTCCTTTCACCATCGATATTGTAATGTCAACTACTAGTGTGGGT      2796

TTATCTATGGCTATAATAAGTTTTTCTTTGTGTTTACTTATGAGTCTTTGTTTTTAATTG      2856
```

FIG. 2C

```
CATGCTAAAAATTGGCAAAAACATATATAATTCTGTTCGTACATGTTTTATTTTATGAAC   2916

TTCATAAGTACCGGTAAAGCAATGATAATGTGTAAAGTTGCTTGGTCTATATATATGTTT   2976

AAATACACATATCTCTAAACCGTCAATGAGAAATACTCTCTGTACCTGTTTATTCAACTT   3036

GGAAAACTAAACCACATAATAAAC (SEQ ID NO:1)                         3060
```

FIG. 2D

Nucleotide Sequence of Enod2b Genomic Clone

```
AAGCTTGACAAAAGATAAATGCTTTGTGGGGTGGCGTAGCGTCTTTATGCAGCAATGGTT    60
Hind3
TATGTAATTTATGTAATGGGGTGGTCACTCCTAGTGACTGTCCTCTGTGTTATGATTAAT   120

GAAATGTTTTGCTTTTTCGAAAAGAACAAAAAATCCTTAAGTTCACCCCATTTGTAAATA   180

GTCTCTTACATTGAATTGGGGTTGAATTATTAAAGAAGAAATCTCAACTACTTATTTATT   240

TTAAATTTCAATCATTTATTAGTTTAATTTTTATAAATCACTTTTCTAAATATTAAAATA   300

TAATAAAACTCTTCTAAAAACATAATAAAATTAATAACTAAAATAAATAAATTATTTTTT   360

ATTGGTATTTATTTTTGTTTTTTTTTTTTCTAAATTCATATTCTTTTACTTATGTTTTAA   420

TAGACAAAAAACTGATTTGTAACNNNNNNCATGTATAGAAAACTATTCCTTTAACCTATA   480

AAAAACTATCATTAAAATATTTTTTAAGATAATTATTATAAAAATCAACAAACTTATTAA   540

TAATATATGATTCAATAATAATATATAAAATCTTTGCATCTAACATAAATTATAATAATA   600

TTACAATTTTTTCCTTTAAATCAATTTTACATTTTAAAAAATCAAATTAAATTCATATCC   660

GACTATTGCTGCGCATGATAGGCTCTAAAAGACCATCCCATTCACATATTAATATCTTAT   720

TCAACGTTAATCTGTGTTCTGTTAGATTCCAAAGATTCCAGTGAATAGTGATGGCTAAGA   780

ACAGTTTCTTGACCTTTCGCTAACAAGCAAGCCTACCTATACAAGCTCCAATTATTTTCT   840

TTTTTGAGGATTGCTCCATTTATTNNCCGACAAAACATACATGCATCTAAATGTGGCAGC   900

ATGCTAAAGTTTTGGTGAGGCTATAGTAAAATATGAAATAAAGATTTGAAGTTTCAGCCC   960

AATATAAAAAAAAATTAATTCCTTCTGAAATGAAAAGAGTATCAAAGAAGATATAATCA  1020
```

FIG. 3A

```
GTAAAATCTTTTTCATAAGCATTGATCTGGATACATCAACTTTGATGCGTTGGAAATACT    1080

GTGCTCAAGTTTGACAGCAATTCTTGGAATTTTTTCGCCACAACAGAAGCTCCAGACGAT    1140

TATGATTTATGACCTTATATGATGTTAGTTACGTGAAAGTAATTAGAATCGCATTTGCTA    1200

ACTATTAGCAATTTTTTTTTTAAGCTAATGCAAGTGACAGAATCTTAGGTCTCTATAAT    1260

TTGAACCTGTGGCGGTGGAACTCGTACTTCATGTGCTGAAAAGAACTTGATATTTTTTA    1320

AGGGAAATAATATATATCAATGCTCCTAAGTCCTAAACTTTATCTTCTTTGGCAGCTAAA    1380

TTTACTTTAAAAAGAAATAAGATTAAATAACTTTTCTTACAAGAAAATATATTTAATTA    1440

TTAATTGTTAAGTTTAACGTCTTTTTATACATTTATTTGTTTTAAATTCCAGTCATCTTT    1500

TTAACATAATTCCAATCATTTATTAGTTTTACTTTTATAAACAATAAAACATAATTAATT    1560

TTCAGATTAAAAAATAGATAGAAGTTTTTTAATTGTTTTTTATTATCAAATTTCAATTTT    1620

AACATATTTTATAATAGATAAAATGAATTGTAACAAATTAATGATTGACCTTATAGATAA    1680

GTAATTTAGCCAACAACTTTTTTAGTATTAAATTGATAGAAAAATTAAGCTATATTTGGG    1740

GGGGGGGGGGGTCAAGTTTAATGAAGTTAAAGTTCATTGAATATATTTGTAAAAAAGAT    1800

AAAGGGTTTAAGGTCTAATAGAGATAATATTTAAGGACTTAATTAATTATTTGATCTTTA    1860
                                                        Sau3a
TACTTGTATTTTTTTTTTGTTTTAGTTTCTATACTTAAAAATTCTGTTTTATTATTTTTA    1920

CGCCTTAGTTTTCTAGCAATCTAAAACTGATATAAAATAGAAGTATAACGACTAAAACAT    1980

AAAAAAAAAAAATTGTATAAAAAATAAAGCATATAGCTTTCATTCATATATAAGAACTAA    2040

ACTGAAATACCAGTGTAAGTATAAGAACTAATCGATAAATTAAGCCAAATTAAGGGTACA    2100
```

FIG. 3B

```
TATTATTTTTAAGAAAATTAGGCCGGGTATATATTTTTAAAAAGGACTATACACTATGTG        2160

ACGATAGAAATAATAGGTATGTAGATGTATGTTAAGTATTTTCTAATGTGTTTTTTACTT        2220

TCTCTATCACACTTGTTATTTTCTCACTATTTTTTTCTCTTGTTTCTCTGTTATTTTCAC        2280

TCTAAAACTGGAGTAATATGTTTATGACTACAACACATTTTGACATGACTTAGGATTAAC        2340

ATATATTATGATAAAATAACTAAAGATTGATAACCTTGATAGAAGCTTCTCATGTCTCCT        2400
    TS ± 20                                  Hind3

CTCCCTATAAGTAGTTTCCCATTGTTATCACTTTTCATCAGCACAAGCTAAGACATGACT        2460
                                                        ORF1  M   T

TCTGTACTACACTACTCACTCCTGCTGCTCCTGCTTGGAGTGGTGATTCTCACCACTCCA        2520
 S   V   L   H   Y   S   L   L   L   L   L   G   V   V   I   L   T   T   P

GTGCTAGCTAATTTGAAGCCACGCTTCTTCTATGAGCCTCCTCCAATTGAGAAACCCCCC        2580
 V   L   A   N   L   K   P   R   F   F   Y   E   P   P   P   I   E   K   P   P
                                  ORF2  M   S   L   L   Q   L   R   N   P   P

ACCTATGAACCTCCACCATTTTATAAGCCCCCATACTACCCACCACCAGTGCACCACCCT        2640
 T   Y   E   P   P   P   F   Y   K   P   P   Y   Y   P   P   P   V   H   H   P
 P   M   N   L   H   H   F   I   S   P   H   T   T   H   H   Q   C   T   T   L

CCACCAGAGTACCAACCACCCCATGAAAAAACACCACCTGAGTATCTACCTCCTCCTCAT        2700
 P   P   E   Y   Q   P   P   H   E   K   T   P   P   E   Y   L   P   P   P   H
 H   Q   S   T   N   H   P   M   K   K   H   H   L   S   I   Y   L   L   L   M

GAGAAACCACCACCAGAATACCTACCTCCTCATGAGAAACCGCCACCAGAATACCAACCT        2760
 E   K   P   P   P   E   Y   L   P   P   H   E   K   P   P   P   E   Y   Q   P
 R   N   H   H   Q   N   T   Y   L   L   M   R   N   R   H   Q   N   T   N   L

CCTCATGAGAAACCACCCCATGAGAATCCACCACCGGAGCACCAACCACCTCATGAGAAG        2820
 P   H   E   K   P   P   H   E   N   P   P   P   E   H   Q   P   P   H   E   K
 L   M   R   N   H   P   M   R   I   H   H   R   S   T   N   H   L   M   R   S

CCACCAGAGCACCAACCACCTCATGAGAAGCCACCACCAGAGTATGAACCACCTCATGAG        2880
 P   P   E   H   Q   P   P   H   E   K   P   P   P   E   Y   E   P   P   H   E
 H   Q   S   T   N   H   L   M   R   S   H   H   Q   S   M   N   H   L   M   R

AAACCACCACCAGAATACCAACCACCTCATGAGAAGCCACCACCAGAATACCAACCACCT        2940
 K   P   P   P   E   Y   Q   P   P   H   E   K   P   P   P   E   Y   Q   P   P
 N   H   H   Q   N   T   N   H   L   M   R   S   H   H   Q   N   T   N   H   L

CATGAGAAACCACCACCAGAATACCAACCACCTCATGAAGCCACCACCAGAGCACCAA        3000
 H   E   K   P   P   P   E   Y   Q   P   P   H   E   K   P   P   P   E   H   Q
 M   R   N   H   H   Q   N   T   N   H   L   M   R   S   H   H   Q   S   T   N
```

FIG. 3C

```
CCACCTCATGAGAAGCCACCAGAGCACCAGCCACCTCATGAGAAGCCACCACCAGAGTAT    3060
 P  P  H  E  K  P  P  E  H  Q  P  P  H  E  K  P  P  P  E  Y
  H  L  M  R  S  H  Q  S  T  S  H  L  M  R  S  H  H  Q  S  I
CAACCACCTCATGAGAAACCACCACCAGAATACCAACCTCCTCAAGAAAAGCCACCACAT    3120
 Q  P  P  H  E  K  P  P  P  E  Y  Q  P  P  Q  E  K  P  P  H
  N  H  L  M  R  N  H  Q  N  T  N  L  L  K  K  S  H  H  M  K
GAAAAACCACCGCCAGAATACCAACCTCCTCATGAAAAGCCACCACCAGAACACCAACCT    3180
 E  K  P  P  P  E  Y  Q  P  P  H  E  K  P  P  P  E  H  Q  P
  N  H  R  Q  N  T  N  L  L  M  K  S  H  H  Q  N  T  N  L  P
CCCCATGAAAAGCCACCACCAGTGTACCCACCCCCTTATGAGAAACCACCACCAGTGTAT    3240
 P  H  E  K  P  P  P  V  Y  P  P  P  Y  E  K  P  P  P  V  Y
  M  K  S  H  H  Q  C  T  H  P  L  M  R  N  H  H  Q  C  M  N
GAACCCCCTTATGAGAAGCCACCCCCAGTAGTGTATCCACCTCCTCATGAGAAACCACCC    3300
 E  P  P  Y  E  K  P  P  P  V  V  Y  P  P  P  H  E  K  P  P
   P  L  M  R  S  H  P  Q  *  (SEQ ID NO:6)
ATTTATGAGCCACCGCCATTGGAGAAGCCACCGGTCTACAATCCCCCACCTTATGGCCGC    3360
 I  Y  E  P  P  P  L  E  K  P  P  V  Y  N  P  P  P  Y  G  R
TATCCACCATCCAAGAAAAACTAATAACCACTTGCCTGCGTCACATGTTTTGGTCTACTC    3420
 Y  P  P  S  K  K  N  *  (SEQ ID NO:5)
AAACTTAGACCTGCCCTTTGTCATATAAAGCTTTCTGTTTCTGTTTAAGATCTCAAGTAC    3480
                      Hind3
AATATGTCCCTTCTGCATGCACTACTTCTTCAAAATAAAGGCTTTATGCCTATGTATAAT    3540

ACTCTACTTTAATTCTCCTTTCACCATCGATATTGTAATGTCAACTACTAGTGTGGGTTT    3600

ATCTATGGCTATAATAAGTTTTTCTTTGTGTTTACTTATGAGTCTTTGTTTTTAATTGCA    3660

TGCTAAAAATTGGCAAAAACATATATAATTCTGTTCGTACATGTTTTATTTTATGAACTT    3720

CATAAGTACCGGTAAAGCAATGATAATGTGTAAAGTTGCTTGGTCTATATATATGTTTAA    3780

ATACACATATCTCTAAACCTGTCAATGAGAAATACTCTCTTGTACCTTGTTTATTCAACT    3840

TGGGAGACTAAACCTA    (SEQ ID NO:4)                              3856
```

FIG. 3D

ENOD2 GENE REGULATORY REGION

This application is a continuation of application Ser. No. 09/564,142, filed May 3, 2000 (now abandoned); which is a continuation application of application Ser. No. 08/859,555, filed May 20, 1997 (now abandoned); which was a continuation application of application Ser. No. 08/411,062; filed Mar. 27, 1995 (now U.S. Pat. No. 5,631,358); which was a continuation application of Ser. No. 07/214,297; filed Jul. 1, 1988 (now abandoned).

FIELD OF THE INVENTION

The field of this invention is the area of plant molecular biology in general, and relates in particular to plant genetic engineering by recombinant DNA technology. This invention specifically relates to a soybean early nodulin gene regulatory region which regulates downstream gene expression in a tissue-specific fashion in the developing soybean root nodule after inoculation with *Bradyrhizobium japonicum*.

BACKGROUND OF THE INVENTION

Nitrogen-fixing root nodules of leguminous plants are formed as the result of root infection by rhizobia and subsequent development of a symbiosis between bacteria and plant. The development of the symbiosis is dependent on specific recognition between plant and bacterium, and it requires genetic information from both the plant and the bacteria.

Nodule development displays variation among legumes. Two different types of nodules are recognized, determinant and indeterminant. The nodules of soybean (Glycine max) for example, are determinant and spherical in shape. In contrast, the nodules of alfalfa (*Medicago* spp.), clover (*Trifolium* spp.), and pea (*Pisum sativum*) are indeterminant and elongated in shape. These nodules are also anatomically and metabolically distinct, reflecting differences in the process of nodule development which may be attributable to genetic differences between legumes as well as between the different species of *Rhizobium* which infect them.

In a description of nodule development, Vincent (J. M. Vincent (1980) in *Nitrogen Fixation*, eds. W. E. Newton and W. H. Orme-Johnson (University Park Press, Baltimore, Md., Vol. 2, pp. 103–131) distinguishes between three different stages of nodule formation: preinfection, infection and nodule formation, and nodule function. In the preinfection stage, the *Rhizobium* cells recognize their host plants and attach to root hairs, an event which is followed by root hair curling. In the next stage, the bacteria enter the roots via infection threads while some cortical cells dedifferentiate to form meristem. The infection threads grow toward the meristematic cells. Bacteria are released into the cytoplasm of about half of these cells, and subsequently the bacterial cells develop into bacteroids. In the final stage further differentiation of nodule cells occurs leading up to a nitrogen-fixing nodule.

Nodule-specific proteins, which are only expressed in root nodules, are likely to be associated with the infection process, nodule development, and symbiotic nitrogen fixation. Both proteins of plant origin (nodulins) and of bacteroid origin (bacteroidins) are found in nodules. Nodule-specific proteins have been identified in root preparations of soybean infected with *Bradyrhizobium japonicum* (R. P. Legocki and D. P. S. Verma (1980), supra) and pea (*Pisum sativum*) infected with *Rhizobium leguminosarum* PRE (T. Bisseling et al. (1983) EMBO J. 2:961–966). In each case, a nodule-specific antiserum was used to identify the nodule proteins by immunoprecipitation. Each of these antisera was produced by titration of an antiserum raised against soluble nodule proteins with a root preparation from uninfected plants. The drawbacks to these studies are that the plant or bacterial origin of the nodule-specific proteins could not be established and that the antigenicity of each protein affects the immunological analysis.

In soybean, the in vitro translation products of root nodule polysomes were analyzed with nodule-specific antiserum. Control experiments showed that bacterial RNA was not translated in the in vitro system. At least 18–20 host plant-derived polypeptides were identified having molecular weights in the range of 18–20 kd. These proteins were absent from uninfected roots, bacteroids and free-living *B. japonicum* (R. P. Legocki and D. P. S. Verma (1980) Cell 20:153–163). In addition, bacteroids were isolated and incubated with $^{35}$S methionine to label bacteroid proteins. Two polypeptides cross-reacted with nodule-specific antiserum. The bacteroid excreted polypeptides had molecular weights of about 11 kd (R. C. van den Bos et al. (1978) J. Gen. Microbiol. 109:131–139). Approximately 20 nodule-specific proteins were identified in pea root protein extracts by probing Western protein blots with nodule-specific antiserum. The proteins detected ranged in molecular weight from 15 to 120 kd; however the origin of these proteins was not determined. In these experiments the in vivo nodule proteins were identified (T. Bisseling et al. (1983), supra), while the soybean study analyzed potentially truncated products of in vitro translation.

Verma and co-workers have also isolated soybean nodulin cDNA clones (F. Fuller et al. (1983) Proc. Natl. Acad. Sci. USA 80:2594–2598). Those clones were used to hybrid select NOD mRNAs from nodule RNA preparations; mRNAs of about 1150, 770, and 3150 nucleotides in length yielded in vitro translation products of 27, 24, and 100 kDa, respectively. Two additional clones, which shared some homology with each other, hybrid selected mRNAs of 1600 and 1100 nucleotides in length with in vitro translation products of 23.5 and 24.5 kDa, respectively (F. Fuller and D. P. S. Verma (1984) Plant Mol. Biol. 3:21–28) were identified.

Nodule mRNA from different stages of developing pea nodules was studied by in vitro translation of the RNA followed by separation of translation products by two dimensional gel electrophoresis. Twenty-one nodule-specific proteins were found, with molecular weights ranging from 15 to 80 kDa (F. Govers et al. (1985) EMBO J. 4:861–867).

Among the nodulins with known functions are leghemoglobin (C. A. Appleby (1984) Ann. Rev. Plant Physiol. 35:443–478), a nodule-specific glutamine synthetase (J. V. Callimore et al. (1983) Planta 157:245–253), and a nodule-specific form of uricase (M. Bergmann et al. (1983) EMBO J. 2:2333–2339). The functions of most nodulins have not been defined. Nodulins may have specific functions in the formation of nodule tissue after the dedifferentiation and proliferation of cortical cells, in the transport of substrates to the bacteroids, in the assimilation of ammonia excreted by the bacteroids, or in the senescence of nodule tissue.

A cDNA library prepared from mature (21 day) soybean root nodules infected with *Bradyrhizobium japonicum* has been analyzed for copies of mRNA transcripts of early (7 day) nodulin genes (Franssen et al. (1987) Proc. Natl. Acad. Sci. USA 84:4495–4499). These genes are expressed while the nodule structure is being formed. pEnod2, the cDNA clone whose insert encodes nodulin-75 (N-75) was sequenced. The 998 bp insert includes a short poly(A) tail, and encodes a proline-rich protein. Nodule mRNA of about 1200 nucleotides in length was hybrid-selected and translated in vitro to give two polypeptides each with an Mr of about 75 kDa. The coding capacity of the mRNAs is significantly less than 75 kDa, but proline-rich proteins, such as collagen, are known to have anomalous behavior on polyacrylamide gels (J. W. Freytag et al. (1979) Biochemistry 18:4761–4768). N-75 expression was first detected at day 7 of nodule development, when nodule meristem emerges through the root epidermis with apparent expression increasing up to about day 13. Expression was observed in R. fredii-induced ineffective nodules without infection threads or bacteroids, so N-75 is likely to be involved in nodule morphogenesis rather than in the infection process per se (H. Franssen et al. (1987) Proc. Natl. Acad. Sci. USA 84:4495–4599).

There is a growing understanding of the DNA sequence elements which control gene expression. The following discussion applies to plant genes which are transcribed by polymerase II. There are known sequences which direct the initiation of mRNA synthesis, those which control transcription in response to environmental stimuli, those which modulate the level of transcription and there are those which regulate gene expression in a tissue-specific fashion.

Promoters are the portions of DNA sequence at the beginnings of genes, which contain the signals for RNA polymerase to begin transcription so that protein synthesis can then proceed. Eukaryotic promoters are complex, and are comprised of components which include a TATA box consensus sequence in the vicinity of −30 relative to the transcription start site (+1) (R. Breathnach and P. Chambon (1981) Ann. Rev. Biochem. 50:349–383; C. Kuhlemeier et al. (1987) Ann. Rev. Plant Physiol. 38:221–257). In plants there may be substituted for the CAAT box a consensus sequence which J. Messing et al. (1983) in *Genetic Engineering of Plants*, T. Kosuge, C. Meredith, and A. Hollaender, eds., have termed the AGGA box, positioned a similar distance from the cap site (+1). Other sequences in the 5' regions of genes are known which regulate the expression of downstream genes. There are sequences which participate in the response to environmental conditions, such as illumination, nutrient availability, hyperthermia, anaerobiosis, or the presence of heavy metals. There are also signals which control gene expression during development, or in a tissue-specific fashion. Promoters are usually positioned 5' to, or upstream of, the start of the coding region of the corresponding gene, and the DNA tract containing the promoter sequences and the ancillary promoter-associated sequences affecting regulation or the absolute levels of transcription may be comprised of less than 100 bp or as much as 1 kbp.

As defined by G. Khoury and P. Gruss (1983) Cell 22:313–314, an enhancer is one of a set of eukaryotic promoter-associated elements that appears to increase transcriptional efficiency in a manner relatively independent of position and orientation with respect to the nearby gene. The prototype enhancer is found in the animal virus SV40. Generally animal or animal virus enhancers can function over a distance as much as 1 kbp 5', in either orientation, and can act 5' or 3' to the gene. The identifying sequence motif (5'-GTGGAAA(orTTT)G-3') is generally reiterated. There have been sequences identified in or adjacent to plant genes which have homology to the core consensus sequence of the SV40 enhancer, but the functional significance of these sequences in plants has not been determined.

There are also reports of enhancer-like elements 5' to certain constitutive and inducible genes of plants. J. Odell et al. (1985), Nature 313:810–812, describe a stretch of about 100 bp 5' to the start site of the CaMV 35S transcript which is necessary for increasing the level of expression of a reporter gene in chimeric constructions. Two different transcription activating elements which can function in plants are derived from the 780 gene and the ocs gene of Aprobacterium tumefaciens T-DNA (W. Bruce and W. Gurley (1987) Mol. Cell. Biol. 7:59–67; J. Ellis et al. (1987) EMBO J. 6:11–16). Regulated enhancer-like elements include those believed to mediate tissue-specific expression and response to illumination (M. Timko et al. (1985) Nature 318:579–582; H. Kaulen et al. (1986) EMBO J. 5:1–8; J. Simpson et al. (1985) EMBO J. 4:2723–2729; J. Simpson et al. (1986) Nature 323:551–554; R. Fluhr et al. (1986) Science 232: 1106–1112).

The molecular mechanisms which regulate the expression of nodulin genes are not yet defined. V. P. Mauro et al. (1985) Nucleic Acids Res. 13:239–249, have analyzed the 5' flanking sequences of three nodulin genes of soybean for conserved DNA sequence motifs. They found three conserved sequence motifs: consensus sequence a 5'-GTTTC-CCT-3', consensus sequence b 5'-GGTAGTG-3', and consensus sequence c 5'-TCTGGGAAA-3'. Whether these sequences function in the regulation of the nodulin genes is not known, and if they do, the stimuli which elicit expression are not known. The molecular mechanisms controlling the expression of Enod2 genes in soybean are also not known, but F. Govers et al. (2986) Nature 323:564–566, have shown that in developing pea root nodules, *Rhizobium leguminosarum* nod genes or adjacent genes carried on a 10 kb region of the Sym plasmid are involved in inducing an early nodulin gene which is homologous to the Enod2 gene of soybean.

Jensen et al. (1986) Nature 321:669–674, transformed the wild legume *Lotus corniculatus* with a Leghemoglobin-CAT chimeric construct. Roots were infected with a strain of *Agrobacterium rhizogenes*, and transformed plants containing the hybrid gene were obtained. Upon infection with *Rhizobium loti*, nodules were formed that expressed the introduced CAT gene in a fashion that was correct by all criteria applied.

SUMMARY OF THE INVENTION

The work of the present invention describes the isolation and characterization of DNA sequences functional in soybean, each of which regulates the expression of a downstream structural gene during the early stages of soybean root nodule development after inoculation with *Bradyrhizobium japonicum*. These regulatory regions are unlike previously described regulatory regions from nodulin genes in that they direct expression earlier in nodule development than other nodulin genes. These regulatory regions are those of early nodulin genes (Enod2).

The Enod2 gene, encodes a nodulin-75, a polypeptide with an apparent molecular weight of about 75 kDa expressed during the early stages of nodule development. The Enod2a regulatory region extends about 1 kb 5' from the start of transcription of the gene. All the signals required for tissue-specific regulated gene expression are contained within this 1000 bp 5' flanking region. The Enod2a regulatory region controls the expression of a downstream structural gene in a tissue-specific manner in the cortex of developing soybean nodule early in the nodule development process.

Example of tissue-specific early nodulin regulatory regions are found in the 5' flanking region of the soybean (Glycine max) Enod2a and Bnod2b genes which encode N-75. The Enod2a regulatory region extends about 1 kb 5' from the transcription start of the sends. The regulatory region contains the nucleotide sequence from FIG. 2 extending from about nucleotide 520 to about nucleotide 1565. The Bnod2b regulatory region extends about 1 kb 5' from the transcription start of the gene, from about nucleotide 1320 to about nucleotide 2365, as in FIG. 3. These regulatory regions direct the expression of a downstream gene in a tissue-specific manner in the developing root nodule.

An additional example of a tissue-specific early nodulin gene regulatory region is the DNA sequence common to the 5' flanking regions of the soybean Enod2a and Enod2b genes. This regulatory element contains DNA sequence as given in FIG. 2, extending from about nucleotide 1050 to about nucleotide 1565, or given in FIG. 3, extending from about nucleotide 1850 to about nucleotide 2365. This regulatory region directs the expression of a downstream structural gene in a tissue-specific manner in the developing root nodule.

A primary object of this invention is to enable those skilled in the art to achieve tissue-specific gene expression in soybean root nodules. This object is accomplished by utilizing a DNA sequence, designated an Enod2 regulatory region. This regulatory region directs the expression of a downstream structural gene during the early stages of nodule development. The term Enod2 regulatory region is used generically to designate the nodule specific regulatory region of any Enod2 gene. The Enod2 regulatory region contains promoter sequences as well as promoter-associated sequences which function in the regulation of the expression of a downstream structural gene.

The invention provides recombinant DNA molecules which comprise an Enod2 regulatory region and a plant-expressible structural gene, wherein said structural gene is positioned 3' to said regulatory region and under its regulatory control, with the result that the structural gene is expressed in the developing soybean root nodule. In general, any structural gene, including gene fusions, that is expressible in a plant can be employed in the recombinant DNA molecules of the present invention.

The recombinant DNA molecules of the present invention are useful in a method for selectively expressing a desired plant-expressible structural gene in a developing nodule of soybean root. In such a method, a soybean plant is genetically transformed to contain the recombinant DNA molecules of the present invention, which contain an Enod2 regulatory region and the desired structural gene which is positioned such that it is under the regulatory control of the Enod2 regulatory element. A soybean plant thus transformed expresses the desired structural gene in a tissue-specific manner in developing nodules. Specifically, nodule-specific expression of the desired structural gene can be achieved by introducing the recombinant DNA molecules of the present invention into soybean tissue and regenerating a soybean plant from the transformed tissue. The recombinant DNA molecules of the present invention are particularly useful for the tissue-specific expression of foreign structural genes not naturally occurring in soybean. Transformation of plant cells and tissue with exogenous or foreign DNA and regeneration of plants from transformed cells or tissue can be achieved by any means known to the art.

BRIEF DESCRIPTION OF THE FIGURES

FIG. 2A-D provides the nucleolide sequence of the Enod2a genomic clone (SEQ ID NO:1) and the amino acid sequences for SEQ ID NOs:2–3.

FIG. 3A-D provides the nucleotide sequence of the Enod2b genomic clone (SEQ ID NO:4) and the amino acid sequences for SEQ ID NOs:5–6.

BRIEF DESCRIPTION OF THE SEQUENCES

Figure 1:
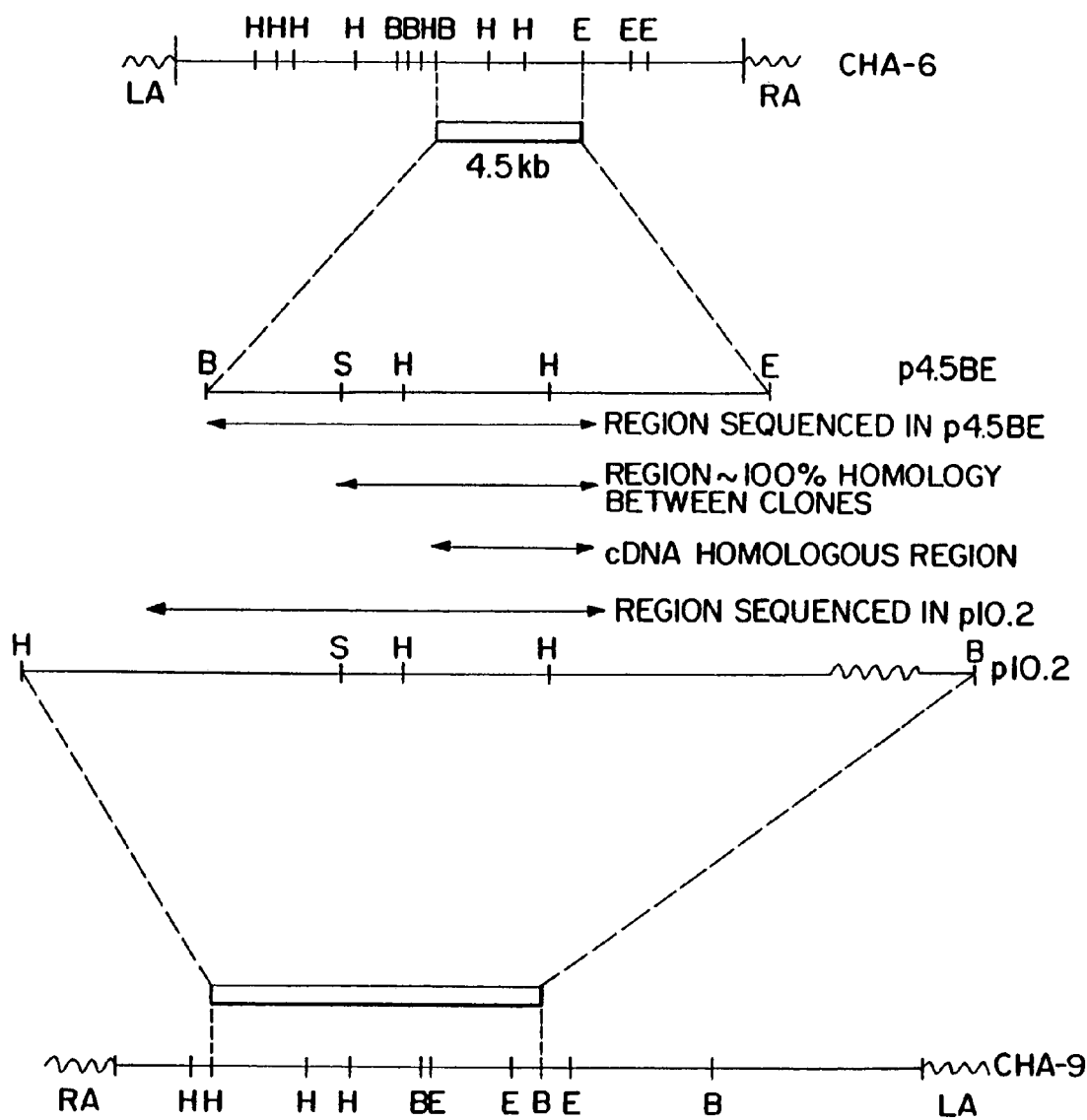
FIG. 1 gives a schematic restriction endonuclease map of the soybean Enod2a and Enod2b genes, and the regions which flank them. Schematic diagrams of CHA-6 (containing the Enod2a gene) and CHA-9 (containing the Enod2b gone) are given. The regions sequenced of both clones are provided in FIGS. 2A–2D (Enod2a; DNA is SEQ ID NO:1; encoded polvoentides are SEQ ID NO:2 and SEQ ID NO:3) and FIGS. 3A–3D (Enod2b: DNA is SEQ ID NO:4: encoded polypeptides are SEQ ID NO:5 and SEQ ID NO:6). The region of approximately 100% homology between the two genomic clones, as well as the regions of the clones homologous to the Enod2 cDNA clone, cap be determined by alignment. Restriction endonucleases are labelled as follows: H-HindIII, B-BamHI, S-Sau3A, E=EcoRI.

SEQ ID NO:1 is the nucleotide sequence oflhe Enod2a genomic clone in FIG. 2A-D.

SEQ ID NO:2 is the amino acid sequence encoded by nucleotides 1654–2494 of SEQ ID NO:1.

SEQ ID NO:3 is the amino acid sequence encoded by nucleotides 1751–2678 of SEQ ID NO:1.

SEQ ID NO:4 is the nucleodde sequence of the Enod2b genomic clone in FIG. 3A-D.

SEQ ID NQ:5 is the amino acid sequence encoded by nicleotides 2456–3264 of SEQ ID NO:4.

SEQ ID NO:6 is the amino acid sequence encoded by nucleotides 2553–3380 of SEQ ID NO:4.

DETAILED DESCRIPTION OF THE INVENTION

The following definitions are provided, in order to remove ambiguities to the intent or scope of their usage in the specification and claims.

The Enod2 gene described herein is an early nodidin gene of soybean (Glycine max), which encodes nodulin polypeptides with an apparent molecular weight of about 75 kDa, noduim 75 (N-75). Two such genes are exemplified by the Enod2a and Enod2b genes which are identified by the DNA sequences given in FIGS. 2A–D and 3A–D respectively.

The Enod2 regulatoTy region is the DNA sequence 5' and adjacent to the Enod2 coding sequence, which includes promoter sequences and promoter-associated sequences and controls tisue-specillc expression of the Enod2 genes in soybean. The regulatory region extends about 1 kb upstream from the transcription start site of an Enod2 gene. All the signals required from tissue-specific regulated gene expression are contained an the approximately 1 kb 5' flanking region. Within this stretch of DNA are sequences with homology to the TATA and CAAT consensus sequences of eukaryotic promoters, and the nodulin gene oonsensus sequences a and c (V. P. Mauro et al. (1985) supra), which are believed to be involved in the regulation of the expression of nod genes expressed later than Enod2 during nodulation. There are also sequence motifs with homology to the SV40 enhancer core consensus sequence which are found in the regulatory region of the soybean Enod2a gene. There may also be other sequence elements which modulate the level of gene expression, which respond to stimuli from the *B. japonicum*, or which detenuine the tissue-specific pression in the developing soybean root nodule after inoculation with *Bradyrhizobium japonicum*. The expression of Enod2 genes controlled by the Enod2 regulatory region is tissue-specific in that it ii limited to the cortex of developing soybean root nodules. The Enod2 regulatory region controls early gene expression in the developing root nodule of soybean with expression beginning at about 7 days after seed planting and inoculation. Expression is induced by contact with soybean nodulating bacteria, such as *B. japonioum*. Enod2 gene expression also occurs in the ineffective nodules induced by strains of *Rhizobium fredii*. The Bnod2a regulatory region is a DNA sequence which includes promoter sequences and promoter-associated sequences and controls the expression of the soybean Enod2a gene. The Enod2a regulatory region extends about 1 k:b upstream from the Enod2a gene transcription start. This region is specifically identified by the DNA sequence in FIG. 2A-D from about nuclcotide 520 to about nucleotide 1565. The Enod2b regulatory region is a DNA sequence which includes promoter sequences and promoter-associated sequences and controls the expression of the soybean Enod2b gene. The Enod2b regulatory region extends about 1 kb upstream from the Bnod2b gene transcription start. This region is specifically identified by the DNA sequence in FIG. 3A-D from about nucleotide 1320 to about necleoticle 2365. These regulatory regions direct tissue-specific expression of a downstream structural gene, such that the gene is selectively expressed in the inner cortex of the developing root nodule in soybean. The Enod2 common regulatory region is the DNA sequence extending about 500 bases upstream of the transcription start site of an Bnod2 gene. The Enod2 common regulatory region is exemplified by the homologous sequences of Enod2a and Enod2b extending from about nucleotide 1050 to about nucleotide IS6S (FIG. 2A-D), and about nucleotide 1850 to about nucleotide 2365 (FIG. 3A-D), respectively. This common regulatory region controls tissue-specific expression of downstream genes in the cortex of developing soybean root nodules.

Expression refers to the transcription and translation of a structural gene so that a polypeptide is made. Gene expression may be assessed by direct detection of the protein product, by protein electrophoresis or by immunological methods, for example. Alternatively, expression may be assessed by the detection of the mRNA products of tranacription (i.e. by northern hybridizations). This method is particularly appropriate for the testing of transcriptional regulatory sequences because the effects of processes such as protein degradation are excluded.

Promoter refers to the DNA sequences at the 5' end of a structural gene which direct the initiation of transcription. Promoter sequences are necessary, but not always sufficient, to drive the expression of the downstream structural genes. The promoter itself may be a composite of segments derived from more than one source, naturally occurring or synthetic. Eukaryotic promoters are commonly recognized by the presence of DNA sequence elements homologous to the canonical form 5'-TATAAT-3' (TATA box) about 10–30 bp 5' to the 5' end of the mRNA (cap site, +1). About 30 bp 5' to the TATA box another promoter component sequence is often, but not always, found which is recognized by the presence of DNA sequences homologous to the canonical form 5'-CCAAT-3'. For the purposes of this application, a promoter is considered to extend about 100 bp 5' from the transcription start site. Promoter-associated sequence elements located further upstream from –100, or within the region between –100 and +1, may contribute to, or exert regulatory control and may determine the relative levels of gene expression. DNA sequences associated with regulatory control of gene expression can extend about 1 kb upstream of the transcription start site of a gene. There may also be additional promoter-associated sequences between +1 and the translation start site which contribute to gene regulation either at the transcriptional or the translational level.

Structural gene refers to that portion of a gene comprising a DNA segment coding for a protein, polypeptide or portion thereof, possibly including a ribosome binding site and/or a translational start codon, but lacking at least one component which drives the initiation of transcription. The term can also refer to copies of a structural gene naturally found within a cell but artificially introduced. The structural gene may encode a protein not normally found in the plant cell in which the gene is introduced, in which case it is termed a foreign structural gene. A foreign structural gene may be derived in whole or in part from a bacterial genome or episome, eukaryotic nuclear or plastid DNA, cDNA, viral DNA, or chemically synthesized DNA. It is further contemplated that a structural gene may contain one or more modifications in either the coding segments or in the untranslated regions which could affect the biological activity or the chemical structure of the expression product, the rate of expression or the manner of expression control. Such modifications include, but are not limited to, insertions, deletions, and substitutions of one or more nucleotides. The structural gene may constitute an uninterrupted coding sequence or it may include one or more introns, bounded by the appropriate splice junctions functional in plants. The structural gene may be a composite of segments derived from one or more sources, naturally occurring or synthetic. That structural gene may also produce a fusion protein. In this application a structural gene is considered to include the polyadenylation signal downstream from the translation termination codon. That polyadenylation signal usually results in the addition of polyadenylic acid tracts to the 3' ends of the precursor mRNAs. It is also known that a canonical polyadenylation signal may cause a cleavage of the transcript and not poly(A) addition Per se (C. Montell et al. (1983) Nature 305:600). It is contemplated that the introduction into plant tissue recombinant DNA molecules containing the Enod2 regulatory region/structural gene complex will include constructions wherein the structural gene and the regulatory region are not derived from the same source (heterologous constructions). Such constructions can include those wherein additional copies of a gene naturally expressed in a plant tissue, but not regulated as an Enod2 gene, are transcribed under the regulatory control of the Enod2 regulatory region. It is understood in the art how to combine the requisite functional elements of regulatory regions and structural genes to achieve gene expression in plant tissue.

Regulatory control refers to the modulation of gene expression by sequence elements upstream of the transcription start site. Regulation may result in an on/off switch for transcription, or it may result in variations in the levels of gene expression. To place a structural gene under regulatory control of sequence elements means to place it sufficiently close to such sequence elements, and in a position relative to such sequence elements so that the gene is switched on or off, or so that its level of expression is measurably varied, as is understood by those skilled in the art. There can also be sequence components in the untranslated leader region of mRNA which contribute to the regulation of gene expression at the translational level.

Chemically synthesized, as related to a sequence of DNA, means that the component nucleotides were assembled in vitro using nonenzymatic means. Manual chemical synthesis of DNA may be accomplished using well established procedures (i.e. M. Caruthers (1983) in *Methodology of DNA and RNA Sequencing*, Weissman (ed.), Praeger Publishers (New York) Chapter 1), or automated synthesis can be performed using one of a number of commercially available machines. Employing the DNA sequence information provided herein, the Enod2 regulatory regions or portions thereof can be synthesized and these synthetic sequences can then be utilized in the construction of the recombinant DNA molecules of the present invention.

Plant tissue includes differentiated and undifferentiated tissues of plants including, but not limited to, roots, shoots, leaves, pollen, seeds, tumor tissue, such as crown galls, and various forms of aggregations of plant cells in culture, such as embryos and calli. The plant tissue may be in planta or in organ, tissue, or cell culture.

Homology as used herein, refers to identity of nucleotide sequences. The extent of homology between DNA sequences can be empirically determined in DNA hybridization experiments, such as those described in B. Hames and S. Higgins (1985) Nucleic Acid Hybridization, IRL Press, Oxford, UK.

pEnod2 was isolated from a cDNA library prepared with 21-day-old soybean root nodule RNA, using RNA from 10-day-old nodules as a probe. Thus, pEnod2 represents an early nodulin cDNA clone. The early nodulin encoded by pEnod2 was identified by hybrid-selecting nodule mRNA and translating in vitro. Two polypeptides, with apparent Mrs of 75000, were found and were each called N-75. The mRNAs homologous to pEnod2 were only about 1200 nucleotides long, with the capacity to encode a protein of at most about 45 kDa. Therefore the soybean-specific insert of pEnod2 was sequenced and the amino acid sequence of N-7S was deduced. Two ORFs of similar size were found (labelled ORF1 and ORF2 FIGS. 2A–D and 3A–D), one with about 20 methionines and the other a proline-rieb sequence, with a repeating heptameric sequence. Because of the anomalous migration on SDS-polyacrylamid. gels and because of the labelling patterns the two N-75s, it was concluded that the proline-rich coding sequence (ORF1) was that of N-7S. It is believed that N-75 is involved in nodule morphogenesis because of its promo content and because of the paUern of expression in the developing nodule. N-75 appears at about day 7 after sowing and inoculation, and increases through day 13; mRNA continues to be present at least through day 21. N-75 is also produced in the developing ineffective nodule of soybean inoculated with *Rhizobium fredii* USDA257. That leads to the conclusion that typical nodule structure with successful infection of the root by rhizobia is not absolutely required for Enod2 expression.

Hybridization studies have shown that there are Enod2 cDNA homologous sequences in *Pisum sativum*, Vicia sativa, Parasponia, and alfalfa. In pea, the nod genes or genes adjacent to the nod genes of *Rhizobium leguminosarum* are known to be involved in the expression of the Enod2-homologous gene (F. Govers et al. (1986) Nature 323:564–566).

Two soybean genomic clones conosponding to pEnod2 have been isolated and the DNA sequences of the coding and flanking regions have been determined FIG. 2A-D and 3A-D). The genes, turned Enod2a and Enod2b, are essentially homologous from about 600bp 5' to the AtG translation start codon through the coding region, which is not interupted by introns, and through some 500 bp of 3' flanking sequence. Comparison of the genomic clones with the Enod2 cDNA sequence indicates that one or both of these gene are expressed in the developing root nodule. S1 mapping of the transcription start site led to the conclusion that the Enod2a start site is at nucleotide 1543.+−0.20 as shown in FIG. 2A-D, and the Enod2b start site is deduced to be similarly located at about nuoleotide 2350, as shown in FIG. 3A-D.

The DNA sequence of the Enod2a gene was analyzed for motifs which are believed to function in transcriptional regulation. A sequence with homology to the canonical TATA box sequence was found at about nucleotide 1490, upstream from the transcription start site (between 1523 and 1563). A CAAT box-homologous sequence was found at about 1478. There were two motifs with homology to the NOD consensus sequence a at about 1450 and 1460, and one sequence motif with homology to the NOD consensus sequence c at about 1550, near the cap site. Within about 1 kb of 5' flanking sequence, there are 5 sequences with homology (up to 2 mismatches) to the enhancer sequence 5'-GTGGTTGT-3', at about 567, 979, 1027, 1377, and 1404.

The functionality of any DNA sequences within the Enod2 regulatory region can be tested by those skilled in the art of plant molecular biology. It will be understood that there may be minor variations within sequences utilized or disclosed in the present application. It is well known in the art that some DNA sequences within a larger stretch of sequence are more important than others in determining functionality. A skilled artisan can test allowable variations in sequence by mutagenic techniques which include, but are not limited to, those discussed by D. Shortle et al. (1981) Ann. Rev. Genet. 15:265; M. Smith (1985) ibid. 19:423; D. Botstein and D. Shortle (1985) Science 229:1193; S. McKnight and R. Kingsbury (1982) Science 217,316; R. Myers et al. (1986) Science 232:613 It is also known how to generate and analyze deletions of varying lengths (e.g. T. Maniatis et al. (1982) *Molecular Cloning*, Cold Spring Harbor Laboratory, Cold Spring Harbor, N.Y.). These variations and others can be determined by standard techniques to enable those of ordinary skill in the art to manipulate and bring into utility the functional units of promoter element and structural genes.

Production of genetically modified plant tissue expressing a structural gene under the transcriptional control of an Enod2 gene regulatory region functional in soybean, or in another species of plant, combines the specific teachings of the present disclosure with a variety of techniques and expedients known in the art. In most instances, alternative expedients exist for each stage of the overall process. The choice of expedients depends on such variables as the choice of the vector system for the introduction and stable maintenance of the expression complex, the plant species to be modified and the desired regeneration strategy, and the particular structural gene to be used. Those of ordinary skill are able to select and use appropriate alternative process steps to achieve a desired result. For instance, although the ultimate starting point for obtaining the plant regulatory element giving tissue-specific expression during the early stages of soybean root nodule development is the Enod2a or Enod2b genes of Glycine max, exemplified in the present application, homologous DNA sequences of other soybean Enod2 genes, or from different sources, could be substituted as long as the appropriate modifications are made to the procedures for manipulating the DNA carrying the Enod2 regulatory region, and provided it is known that the regulation afforded by the alternative sequences is equivalent to that determined by that of the soybean Enod2 gene regulatory region. Homologs Enod2 of structural genes or of other sequences may be identified by the ability of their nucleic acids to cross-hybridize under conditions of appropriate stringency as is well understood in the art.

A principal feature of the present invention is a recombinant DNA molecule having a plant-expressible gene whose expression is controlled by the Enod2 regulatory region of soybean. The expression complex comprises the promoter and promoter-associated sequences of the soybean Enod2 regulatory region and a structural gene expressible in a plant. The regulatory region and the structural gene must be correctly positioned and oriented relative to one another such that the promoter sequences and the promoter-associated regulatory sequence can activate transcription of the structural gene in a tissue-specific fashion in the developing root nodule. To be controlled by the Enod2 regulatory region, the structural gene must be inserted on the 3' side of the regulatory region so that the 5' end of the gene is adjacent to the 3' end of the regulatory region. A polyadenylation signal must be located in the correct orientation downstream from the 3' end of the coding sequence. Another consideration is the distance between the functional elements of the expression complex. Substantial variation appears to exist with regard to these distances; therefore, the distance requirements are best described in terms of functionality. As a first approximation, reasonable operability can be obtained when the distances between functional elements are similar to those in the genes from which they were derived. The distance between the promoter sequences and the 5' end of the structural gene, or between the upstream promoter-associated sequence elements which are responsible for regulatory control and other components in the construction can be varied, and thus one can achieve variations in the levels of expression of the downstream structural gene. In the case of constructions yielding fusion proteins, an additional requirement is that the ligation of the two genes or fragments thereof must be such that the two coding sequences are in the same reading frame, a requirement well understood in the art. An exception to this requirement exists in the case where an intron separates the coding sequence derived from one gene from the coding sequence of the other. In that case, the coding sequences must be bounded by compatible splice sites, and the intron splice sites must be positioned so that the correct reading frame for both genes is established in the fusion after the introns are removed by post-transcriptional processing. It is generally understood in the art how to achieve gene expression in plants, and the skilled artisan will ensure that all necessary requirements are met.

The recombinant DNA molecule carrying the desired structural gene under the control of the Enod2 regulatory region of soybean can be introduced into plant tissue by any means known to those skilled in the art. The technique used for a given plant species or specific type of plant tissue depends on the known successful techniques. As novel means are developed for the stable insertion of foreign genes into plant cells and for manipulating the modified cells, skilled artisans will be able to select from known means to achieve a desired result. Means for introducing recombinant DNA into plant tissue include, but are not limited to transformation (J. Paszkowski et al. (1984) EMBO J. 3:2717), electroporation (M. Fromm et al. (1985) Proc. Natl. Acad. Sci. USA 82:5824), microinjection (A. Crossway et al. (1986) Mol. Gen. Genet. 202:179), or T-DNA mediated transfer from *Agrobacterium tumefaciens* to the plant tissue. There appears to be no fundamental limitation of T-DNA transformation to the natural host range of *Agrobacterium*. Successful T-DNA-mediated transformation of monocots (G. Hooykaas-Van Slogteren et al. (1984) Nature 311:763), gymnosperm (A. Dandekar et al. (1987) Biotechnol. 5:587) and algae (R. Ausich,. EPO Application 108,580) has been reported. Representative T-DNA vector systems are described in the following references: G. An et al. (1985) EMBO J. 4:277; L. Herrera-Estrella et al. (1983) Nature 303:209; L. Herrera-Estrella et al. (1983) EMBO J. 2:987; L. Herrera-Estrella et al. (1985) in Plant Genetic Engineering, New York: Cambridge University Press, p.63. Once introduced into the plant tissue, the expression of the structural gene may be assayed by any means known to the art, and expression may be measured as mRNA transcribed or as protein synthesized. Techniques are known for the in vitro culture of plant tissue, and in a number of cases, for regeneration into whole plants. Several methods are known for the regeneration of soybean tissue. Procedures for transferring the introduced expression complex to commercially useful cultivars are known to those skilled in the art.

The skilled artisan can insert the Enod2 gene, or a chimeric gene comprising the Enod2 regulatory region and a downstream structural gene under the regulatory control of said region, in an *Agrobacterium tumefaciens* T-DNA based vector or an *Agrobacterium rhizogenes* T-DNA based shuttle vector or a which will allow the transfer of the Enod2 gene or the chimeric gene to soybean or to heterologous plant hosts. As will be readily apparent to those of ordinary skill in the art, any plant-expressible gene can be incorporated in place of the Enod2 coding region of the expression complex using any naturally occurring or artificially engineered restriction sites convenient for in vitro manipulations. The major consideration is that the sequences at the junctions remain compatible with transcriptional and translational functionality. The final steps for obtaining genetically modified plant tissue include introducing the expression complex into plant tissue, for example, by inserting the expression complex into a T-DNA-containing vector, and transferring the recombinant DNA to plant tissue wherein the modified T-DNA becomes stably integrated as part of the genome.

The following examples are-provided for illustrative purposes only and are not intended to limit the scope of the invention. The examples utilize many techniques well known and accessible to those skilled in the arts of molecular biology, in the manipulation of recombinant DNA in plant tissue, and in the culture and regeneration of transformed plants. Enzymes are obtained from commercial sources and are used according to the vendors' recommendations or other variations known in the art. Reagents, buffers and culture conditions are also known to the art. References containing standard molecular biological procedures include T. Maniatis et al. (1982) Molecular Cloning, Cold Spring Harbor Laboratory, Cold Spring Harbor, N.Y.; R. Wu (ed.) (1979) Meth. Enzymol. 68; R. Wu et al. (eds.) (1983) Meth. Enzymol. 100 and 101: L. Grossman and K. Moldave (eds.) (1980) Meth. Enzymol. 65; J. Miller (ed.) (1972) Experiments in Molecular Genetics, Cold Spring Harbor Laboratory, Cold Spring Harbor, N.Y.; Old and Primrose (1981) *Principles of Gene Manipulation*, University of California Press, Berkeley, Calif.; R. Schlief and P. Wensink (1982) *Practical Methods in Molecular Biology*; Glover (ed.) (1985) DNA Cloning, Vols. I and II, IRL Press, Oxford, UK; Hames and Higgins (eds.) (1985) Nucleic Acid Hybridization, IRL Press, Ox ford, UK; Setlow and A. Hollaender (1979) *Genetic Engineering: Principles and Methods*, Vols. 1–4, Plenum Press, New York, which are expressly incorporated by reference herein. Abbreviations and nomenclature, where employed, are deemed standard in the field and commonly used in professional journals such as those cited herein.

EXAMPLE 1

Isolation of a cDNA Clone Homologous to the Enod2 Gene

Soybean plants (Glycine max (L) Merr. cv. Williams) were cultured as described for pea plants (T. Bisseling et al. (1978) Biochim. Biophys. Acta 539:1–11) except at 28° C. At the time of sowing, the seeds were inoculated with *Bradyrhizobium japonicum* USDA110. Nodules were excised from the roots with a scalpel. Nodules were frozen in liquid nitrogen and stored at –70° C. until use. Total RNA from nodules and roots was isolated as described (F. Govers et al. (1985) EMBO J. 4:861–867). Poly(A)+was obtained by oligo (dT)-cellulose chromatography and plasmid DNA was isolated by an alkaline lysis procedure (T. Maniatis et al. (1982), supra).

DNA complementary to poly(A)$^+$ RNA isolated from nodules from 21-day-old plants was synthesized with reverse transcriptase (Anglian Biotechnology, Essex, England) and second strand synthesis was performed under standard conditions (Maniatis et al. (1982), supra). The double-stranded cDNA was treated with S1 nuclease (10 units per µg of ds cDNA) and fractionated on a 5–30% sucrose gradient (Beckman SW50 rotor, 47,000 rpm, 6 hr, 4° C.). Double-stranded cDNA with a length of 500 bp or more was tailed with dC and then annealed to PstI-cut oligo(dG)-tailed pBR322 (Boehringer Mannheim) in a 1:1 molar ratio. The hybridized mixture was treated with DNA ligase and used to transform Escherichia coli RR1 (Maniatis et al. (1982), supra).

Individual transformants were picked, transferred to 96 well microtiter plates containing LB medium, 15% glycerol, and 12.5 µg/ml tetracycline, and grown for. 16 h at 37° C. Two replicate filters were made on GeneScreenPlus (New England Nuclear). After 16 hr of bacterial growth on LB agar containing 12.5 µg/ml tetracycline, the filters were prepared for hybridization according to the manufacturer's instructions.

Probes for differential screening were prepared from poly(A)+ RNA isolated from segments of 5-day-old uninfected roots and from nodules 10 days after inoculation. The poly(A)$^+$ RNA was incubated as described for first strand cDNA synthesis except that 10 µCi α-[$^{32}$P]-ATP (specific activity=3200 Ci/mMol; 1 Ci=37 GBq; New England Nuclear) was used. The filters were hybridized as described (H. J. Franssen et al. (1987), supra).

Those clones which specifically hybridized to the 10-day-old nodule poly(A)$^+$ RNA were designated Enod clones because they represent early nodulin genes, which are expressed in the early stages of nodule development. Nod clones are those which represent nodulin genes expressed later during nodule development. pEnod2, which had an insert length of 1000 bp, was chosen for further characterization.

EXAMPLE 2

Identification of pEnod2 as a Gene Encoding an Early Nodulin of About 75 kDa The in vitro translation product of the mRNA homologous to pEnod2 was determined as described (Franssen et al. (1982), supra). The results showed that the pEnod2-encoded polypeptide had an apparent $M_r$ of about 75,000, and an isoelectric point of about 6.5. In accordance with the established nodulin nomenclature (A. van Kammen (1984) Plant Mol. Biol. Rep. 2:43–45), the identified polypeptide was called N-75. After in vitro translation of pEnod2-hybrid-selected mRNA in the presence of [$^3$H]-leucine, a second polypeptide was found which was slightly more basic than the polypeptide which co-migrated with that also labelled with [$^{35}$S]-methionine.

The translation products of the Enod2 mRNAs of about 1200 nucleotides in length have a maximum coding capacity for a polypeptide of only about 45,000. This discrepancy prompted an examination of the DNA sequence of the pEnod2 insert to determine if the deduced amino acid sequence could explain the anomalous size of the encoded proteins. Standard techniques were used for cloning into M13 and pUC vectors (J. Messing (1983) Meth. Enzymol. 101:20–78) and for dideoxy (F. Sanger et al. (1977) Proc. Natl. Acad. Sci. USA 74:5463–5467; M. D. Biggen et al. (1983) Proc. Natl. Acad. Sci. USA 80:3963–3965) and for Maxam-Gilbert sequencing (A. M. Maxam and W. Gilbert (1980) Meth. Enzymol. 65:499–560). The DNA sequence data were stored and analyzed with programs written by R. Staden (R. Staden (1984) Nucleic Acids Res. 12:521–538) on a microVAX/VMS computer.

EXAMPLE 3

Isolation of Genomic Clones Homologous to pEnod2

A soybean (Glycine max cv. Wayne) genomic library, constructed as a Sau3A partial digest in lambdaCH35, was obtained from R. Nagao and J. Key (University of Georgia, Athens, Ga.). E. coli K802$^-$ was used as the host for lambdaCH35 clones. A large number of clones, 10$^5$, representing 2× the soybean genome, were screened for the presence of sequences hybridizing to the radiolabeled pEnod2 probe.

CH6 and CH9 were the two genomic clones which hybridized to the pEnod2 probe. Restriction site mapping on CH6 and CH9 was performed using BamHI, EcoRI, and HindIII (FIG. 1). DNA was digested with restriction enzymes and the fragments were separated by agarose gel electrophoresis and subsequently blotted onto GeneScreen-Plus. Blots were probed with either complete pEnod2 or PstI-HindIII clones prepared therefrom. Restriction fragments containing sequences which hybridized to the pEnod2 were subcloned into pBR322 and propagated in E. coli HB101. p4.5BE contained a 4.5 kb EcoRI fragment from CH6, and p10.2 contained a 10.2 HindIII-BaMHI fragment from CH9.

Subsequently, portions of p4.5BE and p10.2 were suboloned into pUC18 and pUC19 vectors and sequenced as described in Example 2. The DNA sequences of the portions of p4.5BE and p10.2 containing the Enod2 genes are displayed in FIGS. 2A–D and 3A–D. The coding regions and the deduced amino acid sequences of both genes are shown.

EXAMPLE 4

Sequence Analysis of the Enod2a and Enod2b Genes of Soybean

Standard techniques, as described above, were used for the sequencing of the Enod2a and Enod2b genomic sequences. The coding region of each of these genes is an uninterrupted sequence of 930 bp. FIG. 2A-D gives the DNA sequence of the coding region of the Enod2a gene along with about 1650 bp of 5' flanking sequence and about 360 bp of 3' flanking sequence. The coding region and about 600 of 5' flanking sequence of the Enod2b gene is almost identical In sequence to that of the Enod2a gene as shown in FIG. 3A-D; a total of about 2450 of 5' flanking sequence and about 470 bp of 3' flanking sequence of the Enod2b gene are also presented in FIG. 3A-D. It was noted that the two genes were 100% homologous over the coding regions, and almost 100% homologous in the approximately 600 bp of 5' flanking DNA extending to a Sau3A site at positions 1048 in Enod2a and 1852 in Enod2b, and in the 3' flanking DNA that has been sequenced.

Analysis of the sequence of the cDNA clone pEnod2 and the sequences revealed that there were two open reading frames (ORF1 and ORF2) of similar length; both are noted in FIGS. 2A–D and 3A–D. The anomalous migration in SDS-polyacryiamide gel electrophoresia experiments led, in part, to the conclusion that the ORF1 is the actual coding sequence of the Enod2 genes encoding N-75. The polypeptide encoded by ORF1 is rich in proline, and proline-rich polypeptides are known to exhibit aberrant behavior during SDS-polyacrylamide gel electrophoresis (J. W. Freytag et al. (1979), supra). The second line of reasoning was that one of the hybrid-selected translation products was devoid of methionine; ORF1 has only one merhionine codon (at the translation start) while the alternate ORF1 contained about 20 methionine codons, and therefore Its translation product should have been labelled readily with $^{35}S$-methionine.

We claim:

1. A method for expressing a plant-expressible structural gene other than an Enod2 structural gene in a tissue-specific manner in a nodule of a soybean plant said method comprising the steps of introducing a recombinant DNA molecule into a soybean cell, regenerating a transformed soybean plant from said cell, said plant comprising said recombinant DNA molecule, and growing said plant; said recombinant DNA molecule comprising an Enod2 gene regulatory region, wherein the full complement of said regulatory region maintains hybridization with a DNA sequence selected from the group consisting of nucleotides 520 to 1565 of SEQ ID NO:1 and nucleotides 1320 to 2365 of SEQ ID NO:4 under conditions of high stringency, and said plant-expressible structural gene being positioned such that it is expressed under the regulatory control of said regulatory region, wherein said conditions of high stringency are hybridization for 72 hours at 65° C. in 0.9 M NaCl/90 mM sodium citrate, and wash in 0.3 M NaCl/30 mM sodium citrate for 15 minutes at room temperature.

2. The method of claim 1 wherein said Enod2 gene regulatory region is the Enod2a regulatory region of SEQ ID NO: 1.

3. The method of claim 2 wherein said regulatory region comprises the nucleotide sequence as in SEQ ID NO:1 extending from about nucleotide 520 to about nucleotide 1565.

4. The method of claim 1 wherein said regulatory region comprises the nucleotide sequence as in SEQ ID NO:1 extending from about nucleotide 1050 to about nucleotide 1565.

5. The method of claim 1 wherein said method comprises introducing said recombinant DNA molecule into soybean tissue and regenerating said transformed soybean plant from said transformed tissue.

6. The method of claim 1 wherein said structural gene is expressed in the developing root nodule of a soybean plant and wherein said structural gene is expressed in said nodule beginning about 7 days after seed planting.

7. A method for expressing a plant-expressible structural gene, other than an Enod2 structural gene, in a tissue-specific manner in a nodule of a soybean plant, said method comprising the steps of introducing a recombinant DNA molecule into a soybean cell, regenerating a transformed soybean plant from said cell, said plant comprising said recombinant DNA molecule, and growing said plant; said recombinant DNA molecule comprising an Enod2 gene regulatory region, wherein the full complement of said regulatory region maintains hybridization with a DNA sequence selected from the group consisting of nucleotides 1050 to 1565 of SEQ ID NO:1 and nucleotides 1850 to 2365 of SEQ ID NO:4 under conditions of high stringency, said plant-expressible structural gene being positioned such that it is expressed under the regulatory control of said regulatory region, wherein said conditions of high stringency are hybridization for 72 hours at 65° C. in 0.9 M NaCl/90 mM sodium citrate, and wash in 0.3 M NaCl/30 mM sodium citrate for 15 minutes at room temperature.

8. The method of claim 7 wherein hybridization is maintained following a second wash step in 75 mM NaCl/7.5 mM sodium citrate for 30 minutes at 65° C.

* * * * *

UNITED STATES PATENT AND TRADEMARK OFFICE
CERTIFICATE OF CORRECTION

| | |
|---|---|
| PATENT NO. | : 7,214,861 B2 |
| APPLICATION NO. | : 10/751014 |
| DATED | : May 8, 2007 |
| INVENTOR(S) | : Henk J. Franssen and Anton H.J. Bisseling |

It is certified that error appears in the above-identified patent and that said Letters Patent is hereby corrected as shown below:

On the Title page,
Item (75), "Blsseling" should read --Bisseling--.

Column 3,
Line 5, "an Mr of" should read --$M_r$ of--.

Column 4,
Lines 8-9, "Apro-bacterium" should read --Agrobacterium--.

Column 5,
Line 1, "Example" should read --Examples--.
Line 5, "sends" should read --genes--.
Line 8, "Bnod2b" should read --Enod2b--.

Column 6,
Line 9, "polvoentides" should read --polypeptides--.
Line 14, "clone, cap be" should read --clone, can be--.
Line 26, "oflhe" should read --of the--.
Line 32, "nucleodde" should read --nucleotide--.
Line 35, "nicleotides" should read --nucleotides--.
Line 45, "nodidin" should read --nodulin--.
Line 51, "regulatoTy" should read --regulatory--.
Line 61, "oonsensus" should read --consensus--.

Column 7,
Line 3, "detenuine" should read --determine--.
Lines 3-4, "pres-sion" should read --expression--.
Lines 12-13, "B. japoni-oum" should read --B. japonicum--.
Line 18, "about 1 k:b" should read --about 1 kb--.
Line 26, "Bnod2b" should read --Enod2b--.
Line 28, "necleoticle" should read --nucleotide--.
Line 34, "Bnod 2 gene" should read --Enod2 gene--.
Line 37, "IS6S" should read --1565--.

UNITED STATES PATENT AND TRADEMARK OFFICE
CERTIFICATE OF CORRECTION

PATENT NO. : 7,214,861 B2  
APPLICATION NO. : 10/751014  
DATED : May 8, 2007  
INVENTOR(S) : Henk J. Franssen and Anton H.J. Bisseling Page 2 of 2

It is certified that error appears in the above-identified patent and that said Letters Patent is hereby corrected as shown below:

Column 9,  
Line 35, "Mrs" should read --$M_r$s--.  
Line 40, "N-7S" should read --N-75--.  
Line 41, "ORF2FIGS. 2A-D" should read --ORF2 on Figures 2A-D--.  
Line 42, "praline-rieb" should read --proline-rich--.  
Line 44, "SDS-polyacrylamid. gels" should read --SDS-polyacrylamide gels--.  
Line 47, "N-7S" should read --N-75--.  
Line 48, "promo content" should read --proline content--.  
Line 49, "paUern" should read --pattern--.  
Line 64, "conosponding" should read --corresponding--.  
Line 66, "determined FIG. 2A-D" should read --determined (Figures 2A-D--.  
Line 67, "turned Enod2a" should read --termed Enod2a--.

Column 10,  
Line 1, "AtG" should read --ATG--.  
Line 8, "11543. +– 0.20" should read --1543 +– 20--.

Column 16,  
Line 16, "merhionine" should read --methionine--.  
Line 18, "Its translation" should read --its translation--.  
Line 19, "$^{358}$-methionine" should read --$^{35S}$-methionine--.

Signed and Sealed this

Seventh Day of October, 2008

JON W. DUDAS  
*Director of the United States Patent and Trademark Office*

SEQUENCE LISTING

<160> NUMBER OF SEQ ID NOS: 6

<210> SEQ ID NO 1
<211> LENGTH: 3060
<212> TYPE: DNA
<213> ORGANISM: Glycine max

<400> SEQUENCE: 1

```
ggatccttac acaggccaga catccccaag ttctcaaata agacaaattt ggttgttctt      60
ttcttaatat ttcacaggga gatgttctgt cttttgattt ggggatttca tttagcacat     120
aacaaacagt taacaaaatt tcgccccacc aaaaagatgt tgcactagaa ctcaacatag     180
tagctacaac taattctgta aaagttctgt tctttctttc agctttaccg ttcatttcag     240
gtgaatatgg agcagttgtt tcatgtatga ttccatgcaa attataaaac tcattaaaca     300
aactggaatc atactctgtg cctctatcac ttcgaagttt cttaattttc ttattgaatt     360
gattttcaat ttctgttaca aataacttaa acatgtcaag cgcttcactt ttattttca     420 taagatatac atatatatat aatcagagca gtcatcaata aaagtgataa aatatcgttt     480
tccatttctg gtcaacgttc catcaaattc acatatatca gaatgtatta aatccaatgg     540
ctcagattct ttaactactg attttttgtga tttttttagtt attttagatt gactgcaaaa     600
aacacacttt tcaaagtgat ttgaagatag ctttggaata aaacctaagt tactcatatt     660
agatatgcaa cgactattta tatgacaaag tctagaatgc cagaattaaa atcacacagc     720
atgtaagcag aaggagaaac tttattaata tcaagattca atttgaacat gccatcagtg     780
gcgtaccctt tccctacaaa taccccattc ttggtcaaag taaataaatc tgcacctatg     840
gtctgagtaa acccagcctt gtttaaaaga aaaccagaaa ccagattctt tctcatctct     900
ggagtatgca tcacatcttt gagaatcaaa gtctttccag aggtaaactt cagttcaaca     960
tctccagttc tagcaacagt agtggtgtgg gaatcaccca acaacacttt cttattttca    1020
acattcgtgt atgttttaaa catagcatga tctttatact tgtattttt tttgtttta    1080 gtttctatac ttaaaaattc tgttttatta tttttacgcc ttagttttct agcaatctaa    1140
aactgatata aaatagaagt ataacgacta aaacataaaa aaaaaaaatt gtataaaaaa    1200
taaagcatat agctttcatt catatataag aactaaactg aaataccagt gtaagtataa    1260
```

```
gaactaatcg ataaattaag ccaaattaag ggtacatatt atttttaaga aaattaggcc      1320
gggtatatat ttttaaaaag gactatacac tatgtgacga tagaaataat aggtatgtag      1380
atgtatgtta agtattttct aatgtgtttt ttactttctc tatcacactt gttattttct      1440
cactattttt ttctcttgtt tctctgttat tttcactcta aaactggagt aatatgttta      1500
tgactacaac acattttgac atgacttagg attaacatat attatgataa ataactaaa       1560 gattgataac cttgatagaa aagcttctca tgtctcctct ccctataagt agtttcccat      1620
tgttatcact tttcatcagc acaagctaag acatgacttc tgtactacac tactcactcc      1680
tgctgctcct gcttggagtg gtgattctca ccactccagt gctagctaat ttgaagccac      1740
gcttcttcta tgagcctcct ccaattgaga accccccac ctatgaacct ccaccatttt       1800
ataagccccc atactaccca ccaccagtgc caccacctcc accagagtac caaccaccc       1860 atgaaaaaac accacctgag tatctacctc ctcctcatga aaaccacca ccagaatacc      1920 tacctcctca tgagaaaccg ccaccagaat accaacctcc tcatgagaaa cccacccatg      1980
agaatccacc accggagcac caaccacctc atgagaagcc accagagcac caaccacctc      2040
atgagaagcc accaccagag tatgaaccac ctcatgagaa accaccacca gaataccaac      2100
cacctcatga agccaccacc cagaatacca accacctcat gagaaaccac caccagaat       2160 accaaccacc tcatgagaag ccaccaccag agcaccaacc acctcatgag aagccaccag      2220
agcaccagcc acctcatgag aagccaccac cagagtatca accacctcat gagaaaccac      2280
caccagaata ccaacctcct caagaaaagc caccacatga aaaccaccg ccagaatacc       2340 aacctcctca tgaaaagcca ccaccagaac caacctcc ccatgaaaag ccaccaccag        2400
tgtacccacc cccttatgag aaaccaccac cagtgtatga ccccccttat gagaagccac      2460
ccccagtagt gtatccacct cctcatgaga accacccat ttatgagcca ccgccattgg      2520
agaagccacc ggtctacaat cccccaccttt atggccgcta ccaccatcc aagaaaaact      2580 aataaccact tgcctgcgtc acatgttttg gtctactcaa acttagacct gcccttttgtc     2640 atataaagct ttctgtttct gtttaagatc tcaagtacaa tatgtcccttt ctgcatgcac    2700 tacttcttca aaataaaggc tttatgccta tgtataatac tctactttaa ttctcctttc     2760
accatcgata ttgtaatgtc aactactagt gtgggtttat ctatggctat aataagtttt     2820
tctttgtgtt tacttatgag tctttgtttt taattgcatg ctaaaaattg gcaaaaacat     2880
atataattct gttcgtacat gttttatttt atgaacttca taagtaccgg taaagcaatg     2940
ataatgtgta aagttgcttg gtctatatat atgtttaaat acacatatct ctaaaccgtc     3000
aatgagaaat actctctgta cctgtttatt caacttggaa aactaaacca cataataaac      3060
```

<210> SEQ ID NO 2
<211> LENGTH: 309
<212> TYPE: PRT
<213> ORGANISM: Glycine max

<400> SEQUENCE: 2

Met Thr Ser Val Leu His Tyr Ser Leu Leu Leu Leu Leu Gly Val
1               5                   10                  15

Val Ile Leu Thr Thr Pro Val Leu Ala Asn Leu Lys Pro Arg Phe Phe
            20                  25                  30

Tyr Glu Pro Pro Pro Ile Glu Lys Pro Pro Thr Tyr Glu Pro Pro Pro
        35                  40                  45

Phe Tyr Lys Pro Pro Tyr Tyr Pro Pro Pro Val His His Pro Pro Pro
    50                  55                  60

```
Glu Tyr Gln Pro Pro His Glu Lys Thr Pro Pro Glu Tyr Leu Pro Pro
 65                  70                  75                  80

Pro His Glu Lys Pro Pro Glu Tyr Leu Pro Pro His Glu Lys Pro
                 85                  90                  95

Pro Pro Glu Tyr Gln Pro Pro His Glu Lys Pro Pro His Glu Asn Pro
            100                 105                 110

Pro Pro Glu His Gln Pro His Glu Lys Pro Glu His Gln Pro
            115                 120                 125

Pro His Glu Lys Pro Pro Glu Tyr Glu Pro His Glu Lys Pro
        130                 135             140

Pro Pro Glu Tyr Gln Pro His Glu Lys Pro Pro Pro Glu Tyr Gln
145                 150                 155                 160

Pro Pro His Glu Lys Pro Pro Glu Tyr Gln Pro His Glu Lys
                165                 170                 175

Pro Pro Pro Glu His Gln Pro His Glu Lys Pro Pro Glu His Gln
            180                 185                 190

Pro Pro His Glu Lys Pro Pro Glu Tyr Gln Pro His Glu Lys
            195                 200                 205

Pro Pro Pro Glu Tyr Gln Pro Pro Gln Glu Lys Pro Pro His Glu Lys
        210                 215                 220

Pro Pro Pro Glu Tyr Gln Pro His Glu Lys Pro Pro Pro Glu His
225                 230                 235                 240

Gln Pro Pro His Glu Lys Pro Pro Val Tyr Pro Pro Pro Tyr Glu
                245                 250                 255

Lys Pro Pro Val Tyr Glu Pro Pro Tyr Glu Lys Pro Pro Pro Val
            260                 265                 270

Val Tyr Pro Pro Pro His Glu Lys Pro Pro Ile Tyr Glu Pro Pro Pro
        275                 280                 285

Leu Glu Lys Pro Pro Val Tyr Asn Pro Pro Pro Tyr Gly Arg Tyr Pro
        290                 295                 300

Pro Ser Lys Lys Asn
305

<210> SEQ ID NO 3
<211> LENGTH: 239
<212> TYPE: PRT
<213> ORGANISM: Glycine max

<400> SEQUENCE: 3

Met Ser Leu Leu Gln Leu Arg Asn Pro Pro Met Asn Leu His His
 1               5                  10                  15

Phe Ile Ser Pro His Thr Thr His His Gln Cys Thr Thr Leu His Gln
                 20                  25                  30

Ser Thr Asn His Pro Met Lys Lys His His Leu Ser Ile Tyr Leu Leu
             35                  40                  45

Leu Met Arg Asn His His Gln Asn Thr Tyr Leu Leu Met Arg Asn Arg
     50                  55                  60

His Gln Asn Thr Asn Leu Leu Met Arg Asn His Pro Met Arg Ile His
 65                  70                  75                  80

His Arg Ser Thr Asn His Leu Met Arg Ser His Gln Ser Thr Asn His
                 85                  90                  95

Leu Met Arg Ser His His Gln Ser Met Asn His Leu Met Arg Asn His
            100                 105                 110

His Gln Asn Thr Asn His Leu Met Arg Ser His His Gln Asn Thr Asn
```

```
            115                 120                 125
His Leu Met Arg Asn His His Gln Asn Thr Asn His Leu Met Arg Ser
        130                 135                 140

His His Gln Ser Thr Asn His Leu Met Arg Ser His Gln Ser Thr Ser
145                 150                 155                 160

His Leu Met Arg Ser His His Gln Ser Ile Asn His Leu Met Arg Asn
                165                 170                 175

His His Gln Asn Thr Asn Leu Leu Lys Lys Ser His His Met Lys Asn
            180                 185                 190

His Arg Gln Asn Thr Asn Leu Leu Met Lys Ser His His Gln Asn Thr
            195                 200                 205

Asn Leu Pro Met Lys Ser His His Gln Cys Thr His Pro Leu Met Arg
        210                 215                 220

Asn His His Gln Cys Met Asn Pro Leu Met Arg Ser His Pro Gln
225                 230                 235

<210> SEQ ID NO 4
<211> LENGTH: 3856
<212> TYPE: DNA
<213> ORGANISM: Glycine max
<220> FEATURE:
<221> NAME/KEY: misc_feature
<222> LOCATION: (444)..(449)
<223> OTHER INFORMATION: Unknown nucleotide.
<220> FEATURE:
<221> NAME/KEY: misc_feature
<222> LOCATION: (865)..(866)
<223> OTHER INFORMATION: Unknown nucleotide.

<400> SEQUENCE: 4
aagcttgaca aaagataaat gctttgtggg gtggcgtagc gtctttatgc agcaatggtt      60
tatgtaattt atgtaatggg gtggtcactc ctagtgactg tcctctgtgt tatgattaat     120
gaaatgtttt gcttttcga aagaacaaa aatccttaa gttcacccca tttgtaaata       180
gtctcttaca ttgaattggg gttgaattat taaagaagaa atctcaacta cttatttatt     240
ttaaatttca atcatttatt agtttaattt ttataaatca cttttctaaa tattaaaata     300
taataaaact cttctaaaaa cataataaaa ttaataacta aaataaataa attattttt     360 attggtattt attttgttt ttttttttc taaattcata ttcttttact tatgttttaa      420
tagacaaaaa actgatttgt aacnnnnnnc atgtatagaa aactattcct ttaacctata     480
aaaaactatc attaaaatat tttttaagat aattattata aaaatcaaca aacttattaa     540
taatatatga ttcaataata atatataaaa tctttgcatc taacataaat tataataata     600 ttacaattt ttcctttaaa tcaattttac attttaaaaa atcaaattaa attcatatcc      660
gactattgct gcgcatgata ggctctaaaa gaccatccca ttcacatatt aatatcttat     720
tcaacgttaa tctgtgttct gttagattcc aaagattcca gtgaatagtg atggctaaga     780
acagtttctt gacctttcgc taacaagcaa gcctacctat acaagctcca attattttct     840 ttttgagga ttgctccatt tattnnccga caaaacatac atgcatctaa atgtggcagc      900
atgctaaagt tttggtgagg ctatagtaaa atatgaaata aagatttgaa gtttcagccc     960
aatataaaaa aaaattaat tccttctgaa atgaaaagag tatcaaagaa gatataatca    1020
gtaaaatctt tttcataagc attgatctgg atacatcaac tttgatgcgt tggaaatact    1080
gtgctcaagt ttgacagcaa ttcttggaat ttttcgcca caacagaagc tccagacgat    1140
tatgatttat gaccttatat gatgttagtt acgtgaaagt aattagaatc gcatttgcta    1200
```

-continued

| | |
|---|---|
| actattagca attttttttt ttaagctaat gcaagtgaca gaatcttagg tctctataat | 1260 |
| ttgaacctgt ggcggtggaa ctcgtacttc atgtgctgaa agaacttga tattttttta | 1320 |
| agggaaataa tatatatcaa tgctcctaag tcctaaactt tatcttcttt ggcagctaaa | 1380 |
| tttactttaa aagaaataa gattaaataa cttttttctta caagaaaata tatttaatta | 1440 |
| ttaattgtta agtttaacgt cttttttatac atttatttgt tttaaattcc agtcatcttt | 1500 |
| ttaacataat tccaatcatt tattagttttt acttttataa acaataaaac ataattaatt | 1560 |
| ttcagattaa aaaatagata gaagttttttt aattgttttt tattatcaaa tttcaattttt | 1620 |
| aacatattttt ataatagata aaatgaattg taacaaatta atgattgacc ttatagataa | 1680 |
| gtaatttagc caacaacttt tttagtatta aattgataga aaattaagc tatatttggg | 1740 |
| gggggggggg gtcaagttta atgaagttaa agttcattga atatatttgt aaaaaaagat | 1800 |
| aaagggttta aggtctaata gagataatat ttaaggactt aattaattat ttgatcttta | 1860 |
| tacttgtatt tttttttttgt tttagtttct atacttaaaa attctgtttt attatttttta | 1920 |
| cgccttagtt ttctagcaat ctaaaactga tataaaatag aagtataacg actaaaacat | 1980 |
| aaaaaaaaaa aattgtataa aaaataaagc atatagcttt cattcatata taagaactaa | 2040 |
| actgaaatac cagtgtaagt ataagaacta atcgataaat taagccaaat taagggtaca | 2100 |
| tattattttt aagaaaatta ggccgggtat atattttttaa aaaggactat acactatgtg | 2160 |
| acgatagaaa taataggtat gtagatgtat gttaagtatt ttctaatgtg ttttttactt | 2220 |
| tctctatcac acttgttatt ttctcactat ttttttctct tgtttctctg ttattttcac | 2280 |
| tctaaaactg gagtaatatg tttatgacta caacacattt tgacatgact taggattaac | 2340 |
| atatattatg ataaaataac taaagattga taaccttgat agaagcttct catgtctcct | 2400 |
| ctccctataa gtagtttccc attgttatca cttttcatca gcacaagcta agacatgact | 2460 |
| tctgtactac actactcact cctgctgctc ctgcttggag tggtgattct caccactcca | 2520 |
| gtgctagcta atttgaagcc acgcttcttc tatgagcctc ctccaattga gaaacccccc | 2580 |
| acctatgaac ctccaccatt ttataagccc ccatactacc caccaccagt gcaccaccct | 2640 |
| ccaccagagt accaaccacc ccatgaaaaa acaccacctg agtatctacc tcctcctcat | 2700 |
| gagaaaccac caccagaata cctacctcct catgagaaac cgccaccaga ataccaacct | 2760 |
| cctcatgaga accaccccca tgagaatcca ccaccggagc accaaccacc tcatgagaag | 2820 |
| ccaccagagc accaaccacc tcatgagaag ccaccaccag agtatgaacc acctcatgag | 2880 |
| aaaccaccac cagaatacca accacctcat gagaagccac caccagaata ccaaccacct | 2940 |
| catgagaaac caccaccaga ataccaacca cctcatgaga gccaccacc agagcaccaa | 3000 |
| ccacctcatg agaagccacc agagcaccag ccacctcatg agaagccacc accagagtat | 3060 |
| caaccacctc atgagaaacc accaccagaa taccaacctc ctcaagaaaa gccaccacat | 3120 |
| gaaaaccac cgccagaata ccaacctcct catgaaaagc caccaccaga acaccaacct | 3180 |
| ccccatgaaa agccaccacc agtgtaccca ccccttatg agaaaccacc accagtgtat | 3240 |
| gaacccccctt atgagaagcc accccagta gtgtatccac ctcctcatga aaaccacccc | 3300 |
| atttatgagc caccgccatt ggagaagcca ccggtctaca atcccccacc ttatggccgc | 3360 |
| tatccaccat ccaagaaaaa ctaataacca cttgcctgcg tcacatgttt tggtctactc | 3420 |
| aaacttagac ctgcccttttg tcatataaag cttttctgttt ctgtttaaga tctcaagtac | 3480 |
| aatatgtccc ttctgcatgc actacttctt caaaataaag ctttatgcc tatgtataat | 3540 |
| actctacttttt aattctccttt tcaccatcga tattgtaatg tcaactacta gtgtgggttt | 3600 |

-continued

```
atctatggct ataataagtt tttctttgtg tttacttatg agtctttgtt tttaattgca    3660
tgctaaaaat tggcaaaaac atatataatt ctgttcgtac atgtttatt ttatgaactt      3720 cataagtacc ggtaaagcaa tgataatgtg taaagttgct tggtctatat atatgtttaa    3780
atacacatat ctctaaacct gtcaatgaga atactctct tgtaccttgt ttattcaact      3840
tgggagacta aaccta                                                     3856
```

<210> SEQ ID NO 5
<211> LENGTH: 309
<212> TYPE: PRT
<213> ORGANISM: Glycine max

<400> SEQUENCE: 5

```
Met Thr Ser Val Leu His Tyr Ser Leu Leu Leu Leu Leu Gly Val
1               5                   10                  15

Val Ile Leu Thr Thr Pro Val Leu Ala Asn Leu Lys Pro Arg Phe Phe
            20                  25                  30

Tyr Glu Pro Pro Pro Ile Glu Lys Pro Pro Thr Tyr Glu Pro Pro Pro
            35                  40                  45

Phe Tyr Lys Pro Pro Tyr Tyr Pro Pro Val His His Pro Pro Pro
    50                  55                  60

Glu Tyr Gln Pro Pro His Glu Lys Thr Pro Pro Glu Tyr Leu Pro Pro
65                  70                  75                  80

Pro His Glu Lys Pro Pro Pro Glu Tyr Leu Pro Pro His Glu Lys Pro
                85                  90                  95

Pro Pro Glu Tyr Gln Pro Pro His Glu Lys Pro Pro His Glu Asn Pro
            100                 105                 110

Pro Pro Glu His Gln Pro Pro His Glu Lys Pro Pro Glu His Gln Pro
            115                 120                 125

Pro His Glu Lys Pro Pro Pro Glu Tyr Glu Pro Pro His Glu Lys Pro
        130                 135                 140

Pro Pro Glu Tyr Gln Pro Pro His Glu Lys Pro Pro Pro Glu Tyr Gln
145                 150                 155                 160

Pro Pro His Glu Lys Pro Pro Pro Glu Tyr Gln Pro Pro His Glu Lys
                165                 170                 175

Pro Pro Pro Glu His Gln Pro Pro His Glu Lys Pro Pro Glu His Gln
            180                 185                 190

Pro Pro His Glu Lys Pro Pro Pro Glu Tyr Gln Pro Pro His Glu Lys
        195                 200                 205

Pro Pro Pro Glu Tyr Gln Pro Pro Gln Glu Lys Pro Pro His Glu Lys
    210                 215                 220

Pro Pro Pro Glu Tyr Gln Pro Pro His Glu Lys Pro Pro Pro Glu His
225                 230                 235                 240

Gln Pro Pro His Glu Lys Pro Pro Val Tyr Pro Pro Pro Tyr Glu
                245                 250                 255

Lys Pro Pro Pro Val Tyr Glu Pro Pro Tyr Glu Lys Pro Pro Pro Val
            260                 265                 270

Val Tyr Pro Pro Pro His Glu Lys Pro Pro Ile Tyr Glu Pro Pro Pro
        275                 280                 285

Leu Glu Lys Pro Pro Val Tyr Asn Pro Pro Pro Tyr Gly Arg Tyr Pro
    290                 295                 300

Pro Ser Lys Lys Asn
305
```

-continued

```
<210> SEQ ID NO 6
<211> LENGTH: 238
<212> TYPE: PRT
<213> ORGANISM: Glycine max

<400> SEQUENCE: 6

Met Ser Leu Leu Gln Leu Arg Asn Pro Pro Met Asn Leu His His
1               5                   10                  15

Phe Ile Ser Pro His Thr Thr His His Gln Cys Thr Thr Leu His Gln
                20                  25                  30

Ser Thr Asn His Pro Met Lys Lys His His Leu Ser Ile Tyr Leu Leu
            35                  40                  45

Leu Met Arg Asn His His Gln Asn Thr Tyr Leu Leu Met Arg Asn Arg
    50                  55                  60

His Gln Asn Thr Asn Leu Leu Met Arg Asn His Pro Met Arg Ile His
65                  70                  75                  80

His Arg Ser Thr Asn His Leu Met Arg Ser His Gln Ser Thr Asn His
                85                  90                  95

Leu Met Arg Ser His His Gln Ser Met Asn His Leu Met Arg Asn His
            100                 105                 110

His Gln Asn Thr Asn His Leu Met Arg Ser His His Gln Asn Thr Asn
            115                 120                 125

His Leu Met Arg Asn His His Gln Asn Thr Asn His Leu Met Arg Ser
    130                 135                 140

His His Gln Ser Thr Asn His Leu Met Arg Ser His Gln Ser Thr Ser
145                 150                 155                 160

His Leu Met Arg Ser His His Gln Ser Ile Asn His Leu Met Arg Asn
                165                 170                 175

His Gln Asn Thr Asn Leu Leu Lys Lys Ser His His Met Lys Asn His
            180                 185                 190

Arg Gln Asn Thr Asn Leu Leu Met Lys Ser His His Gln Asn Thr Asn
            195                 200                 205

Leu Pro Met Lys Ser His His Gln Cys Thr His Pro Leu Met Arg Asn
    210                 215                 220

His His Gln Cys Met Asn Pro Leu Met Arg Ser His Pro Gln
225                 230                 235
```